(12) United States Patent
Daly et al.

(10) Patent No.: US 6,265,343 B1
(45) Date of Patent: Jul. 24, 2001

(54) CATALYST AND METHOD FOR THE SYNTHESIS OF CHLORINE DIOXIDE, AND METHOD OF MAKING CATALYST FOR THE SYNTHESIS OF CHLORINE DIOXIDE

(75) Inventors: Francis Patrick Daly, Milford; Daniel Ostgard, East Brunswick, both of NJ (US)

(73) Assignee: Degussa Corporation, Parsippany, NJ (US)

( * ) Notice: Subject to any disclaimer, the term of this patent is extended or adjusted under 35 U.S.C. 154(b) by 0 days.

(21) Appl. No.: 08/206,623

(22) Filed: Mar. 7, 1994

(51) Int. Cl.⁷ .............................. B01J 23/02; B01J 23/42; B01J 23/44
(52) U.S. Cl. ..................... 502/339; 502/330; 502/333; 502/334
(58) Field of Search ................................. 502/330, 333, 502/334, 339

(56) References Cited

U.S. PATENT DOCUMENTS

| | | | |
|---|---|---|---|
| 3,974,102 | * | 8/1976 | Kaiser .................................. 502/330 |
| 4,224,192 | * | 9/1980 | Foster et al. ......................... 502/333 |
| 4,492,769 | * | 1/1985 | Blanchard et al. ................... 502/333 |
| 4,757,045 | * | 7/1988 | Turner et al. ......................... 502/334 |
| 5,008,096 | * | 4/1991 | Ringo .................................... 423/477 |
| 5,197,636 | | 3/1993 | Mitchell et al. . |

FOREIGN PATENT DOCUMENTS

| | | |
|---|---|---|
| 0 291 411 | 11/1988 | (EP) . |
| 0 458 006 | 11/1991 | (EP) . |

* cited by examiner

Primary Examiner—Elizabeth D. Wood
(74) Attorney, Agent, or Firm—Smith, Gambrell & Russell, LLP

(57) ABSTRACT

Chlorine dioxide is generated from an aqueous solution of sodium chlorite in the presence of a catalyst having a reduced rate of deactivation. The catalyst is preferably palladium, or palladium together with another platinum group metal (e.g., Pd+Pt), or palladium together with a Group IB metal (e.g., Pd+Au) deposited on a support modified by Group IA carbonate salt (e.g., $K_2CO_3$) or a Group IIA carbonate salt (e.g., $CaCO_3$) or a magnesium salt that can be converted to MgO or a support consisting of a Group IA carbonate salt or a Group IIA carbonate salt or a magnesium salt that can be converted to MgO.

18 Claims, 6 Drawing Sheets

The Effect of Alloying Pd with Au, Ag, and Pt on Catalyst Deactivation

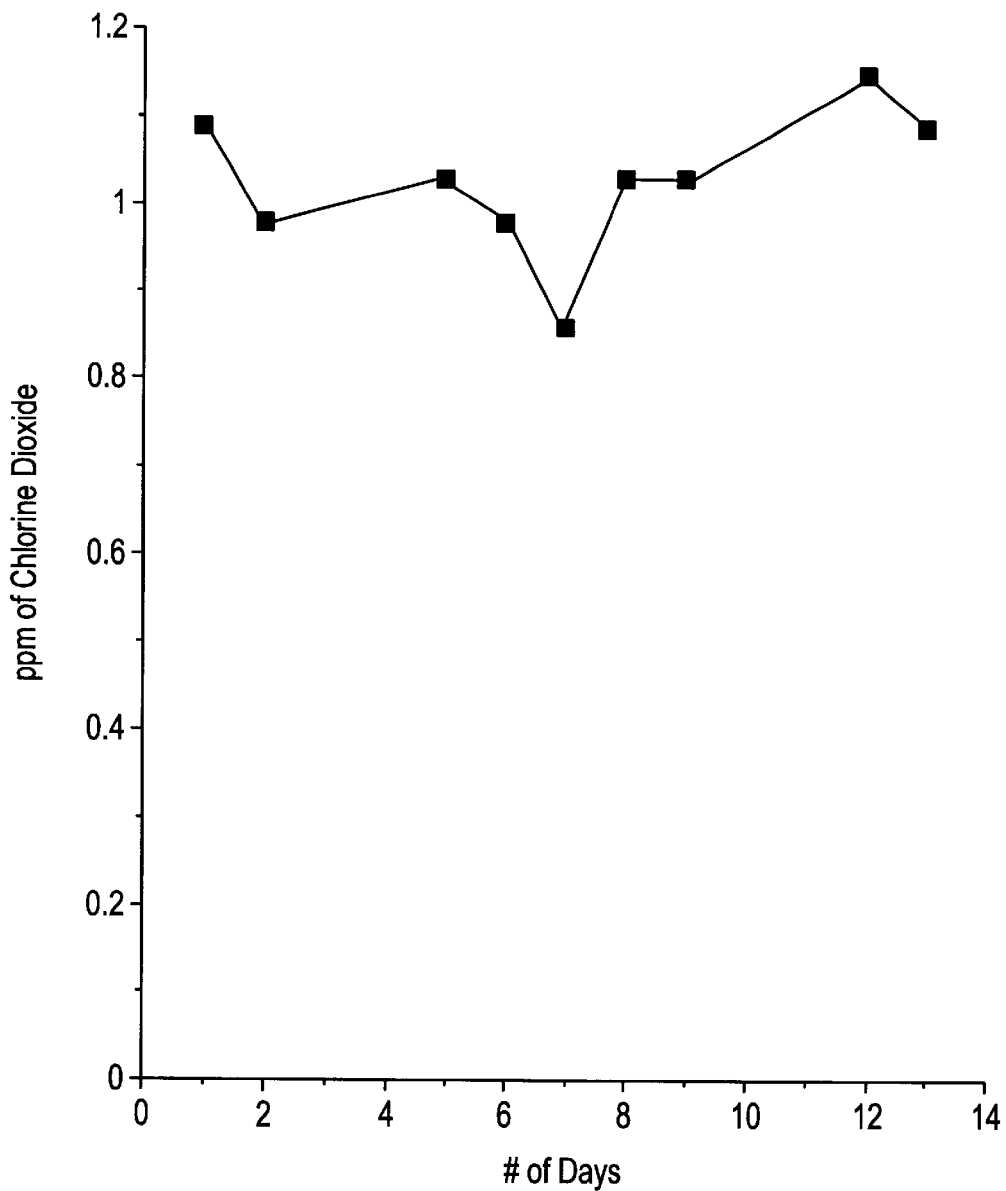

CATALYST AND METHOD FOR THE SYNTHESIS OF CHLORINE DIOXIDE, AND METHOD OF MAKING CATALYST FOR THE SYNTHESIS OF CHLORINE DIOXIDE

BACKGROUND OF THE INVENTION

The present invention relates to a catalyst for the synthesis of chlorine dioxide and to a method of making such a catalyst. The catalyst is preferably palladium, or palladium together with another platinum group metal (e.g., Pd+Pt), or palladium together with a Group IB metal (e.g., Pd+Au) deposited on a support consisting of a Group IA carbonate salt (e.g., $K_2CO_3$) or a Group IIA carbonate salt (e.g., $CaCO_3$) or a magnesium salt that can be converted to MgO or a support modified by Group IA carbonate salt (e.g., $K_2CO_3$) or a Group IIA carbonate salt (e.g., $CaCO_3$) or a magnesium salt that can be converted to MgO. The catalysts of the present invention has a slower rate of deactivation than catalysts previously used for this purpose.

In another aspect, the present invention concerns a method for generating chlorine dioxide from an aqueous solution of a precursor therefor and directing the resulting chlorine dioxide at the material to be disinfected.

Chlorine dioxide is known to act as a disinfecting or sterilizing agent for solutions and devices (e.g., contact lenses). Chlorine dioxide is generally produced from a solution of a chlorine dioxide precursor, such as sodium chlorite solutions, by contacting the solution with a catalyst (e.g., catalysts containing noble metals, as described for example in U.S. Pat. No. 5,008,096). However, known catalysts have the disadvantage of becoming greatly deactivated within a matter of days.

SUMMARY OF THE INVENTION

An object of the present invention is to provide novel chlorine dioxide generating catalysts having a slower rate of deactivation than known catalysts. In achieving the above and other objects, one feature of the invention resides in a catalyst which is composed of a support wherein the outside edge of the support is impregnated with palladium or palladium and another platinum group metal or palladium and a Group IB metal. The support itself is selected from the group of supports modified by a Group IA carbonate salt or a Group IIA carbonate salt or a magnesium salt that can be converted to MgO. Many well known catalyst supports, such as gamma alumina, can be used to form the modified support as described. In another aspect, the Group IA carbonate salt (e.g., $K_2CO_3$) or Group IIA carbonate salt (e.g., $CaCO_3$) or a magnesium salt that can be converted to MgO can be formed into a self sustaining support such as a pellet or honeycomb.

Another object of the present invention is to provide a method of making a catalyst for producing chlorine dioxide having a slower rate of deactivation. The method involves preadjusting the pH of an aqueous solution of palladium or palladium and another platinum group metal or palladium and a Group IB metal salt to a pH range of 1 to 6.3, adding the solution to a slurry of water and a support selected from supports modified by a Group IA carbonate salt or a Group IIA carbonate salt or a magnesium salt that can be converted to MgO or a support consisting of a Group IA carbonate salt (e.g., $K_2CO_3$) or a Group IIA carbonate salt (e.g., $CaCO_3$) or a magnesium salt that can be converted to MgO, maintaining the pH of the slurry from 6 to 10 for several minutes at a temperature of 70° to 90° C., and adding a reducing agent, thereby impregnating the outside edge of the support with palladium or palladium and another platinum group metal or palladium and a Group IB metal.

An additional object of the present invention is to provide a method for generating chlorine dioxide from a chlorine dioxide precursor. The method involves contacting an aqueous medium containing a chlorine dioxide precursor with the above described catalyst.

Another method for generating chlorine dioxide from a chlorine dioxide precursor involves providing a multicompartment container, a first compartment containing a chlorine dioxide precursor, a second compartment containing the catalyst described above, dispelling from the first compartment a quantity of the chlorine dioxide precursor to flow into the second compartment containing the catalyst, contacting the precursor with the catalyst thereby forming chlorine dioxide, and ejecting the chlorine dioxide from the container to the surface of an item to be disinfected or treated.

Furthermore, there is provided a two component package comprising the catalyst described above and a chlorine dioxide precursor.

BRIEF DESCRIPTION OF THE DRAWINGS

The present invention will be further understood with reference to the drawings, wherein:

FIG. 6 is a graph of the performance of a Pd/Au catalyst on a $K_2CO_3$ modified alumina support.

DETAILED DESCRIPTION OF THE INVENTION

Figure 1:
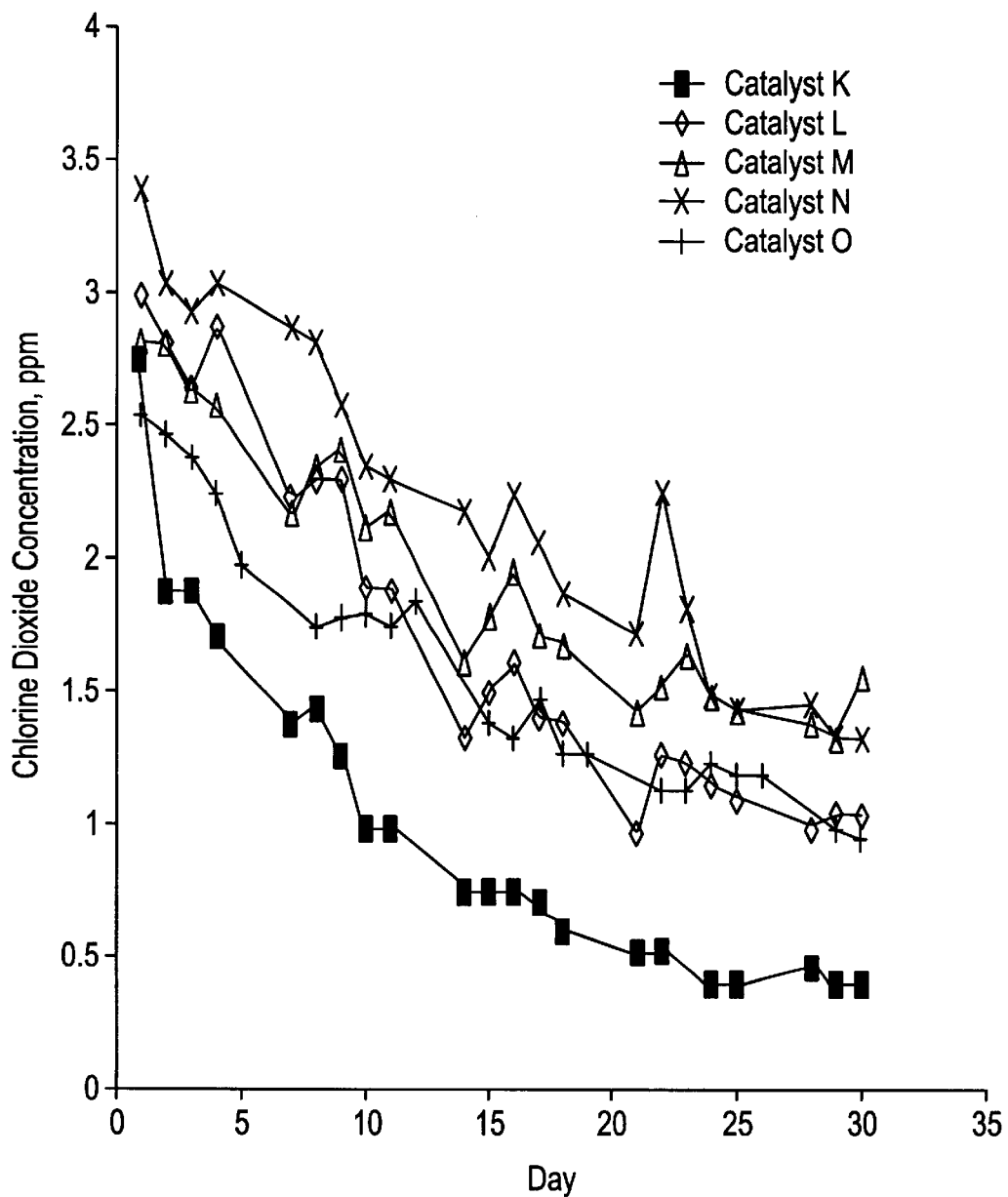
FIG. 1 is a graph of the effect of alloying Pd with Au, Ag or Pt on catalyst deactivation.

A catalyst made for the generation of chlorine dioxide in accordance with this invention is comprised of palladium, or palladium together with another platinum group metal (e.g., Pd+Pt), or palladium together with a Group IB metal (e.g., Pd+Au) deposited on a support modified by a Group IA carbonate salt (e.g., $K_2CO_3$) or a Group IIA carbonate salt (e.g., $CaCO_3$) or a water soluble magnesium salt (e.g., acetate, nitrate, carbonate, chloride) that can be converted to MgO or a support consisting of a Group IA carbonate salt (e.g., $K_2CO_3$) or a Group IIA carbonate salt (e.g., $CaCO_3$) or a water soluble magnesium salt (e.g., acetate, nitrate, carbonate, chloride) that can be converted to MgO. The catalytic metal must be present at a weight % of at least 0.1 and up to 20, preferably 1 to 10, based on the total weight of the catalyst. Palladium is preferred. Aqueous solutions of Group VIII and Group IB metal salts (i.e., halides and nitrates) can be used in the preparation of the catalyst. For example, the following ranges (wt/wt) can be used: ratio of Au to Pd, 0.01:1 to 2:1, preferably 0.2:1 to 0.8:1; ratio of Pt to Pd, 0.01:1 to 2:1, preferably 0.2:1 to 0.8:1.

The support, which is modified by a Group IA carbonate salt (e.g., $K_2CO_3$) or a Group IIA carbonate salt (e.g., $CaCO_3$) or a magnesium salt that can be converted to MgO, may be selected from many well known high surface metallic or ceramic catalyst supports, such as gamma alumina, silica-alumina, silica, titania, etc. Typically, such supports have a surface area of at least about 40 $m^2/g$, preferably 100 $m^2/g$.

The method of making the catalyst is illustrated with palladium, but other platinum group metals or combinations of palladium and another platinum group metal (e.g., Pd+Pt) or combinations of palladium and a Group IB metal (e.g., Pd+Au) can be substituted with comparable results. The catalyst is supported for example on a MgO or $CaCO_3$ or $K_2CO_3$ catalyst support or matrix which is substantially inert when exposed to the conditions used in the enhanced generation of chlorine dioxide from a chlorine dioxide precursor in accordance with the present invention. The support must be thermostable and must provide high support area. The configuration of supports are known in the art. The supported component may have any suitable shape or configuration, such as sheets, rods, extrudates, tablets, pills, irregular shaped particles, spheres, disks, pellets and the like. Monoliths can also be used. The formation of the MgO or $CaCO_3$ or $K_2CO_3$ inert support can be carried out by known means.

Any of a number of conventional techniques can be employed to deposit the platinum group metal(s), or platinum group metal and Group IB metal, on the support material. These techniques include impregnation, co-precipitation, ion-exchange, dipping, spraying, vacuum deposits and the like.

The palladium or palladium and another platinum group metal (e.g., Pd+Pt) or palladium and a Group IB metal (e.g., Pd+Au) can be deposited on the outside edge of the MgO or $CaCO_3$ or $K_2CO_3$ support in a number of ways known in the art. The preferred method is by promoting rapid hydrolysis of the water soluble salts of the noble metals when added to a MgO or $CaCO_3$ or $K_2CO_3$ particulate-water slurry. This can be achieved by preadjusting the pH of the noble metal salt solution to 1 to 6.3, depending on the metal salts used, prior to addition to the slurry. The concentration of the noble metal salt in the aqueous solution is not critical and can vary widely. After that, the process is continued by maintaining the pH of the slurry at 6 to 10 for several minutes at a temperature of 70° to 90° C., prior to the addition of a reducing agent.

The result of following these reaction conditions is that the finely divided MgO or $CaCO_3$ or $K_2CO_3$ particles have the catalytically active metal, e.g., palladium (or Pd+Pt or Pd+Au), deposited on the exterior surface of the particle. The MgO or $CaCO_3$ or $K_2CO_3$ particle can range from 0.0001 to 4 mm in size, preferably 0.001 to 4 mm, though the upper limit is not critical. The penetration of the palladium (or Pd+Pt or Pd+Au) into the MgO or $CaCO_3$ or $K_2CO_3$ particle can be determined by transmission electron microscopy.

Broadly, the method for enhancing generation of chlorine dioxide according to the present invention involves contacting an aqueous medium containing a chlorine dioxide precursor with a catalyst formed of Pd (or Pd+Pt or Pd+Au) deposited on a MgO or $CaCO_3$ or $K_2CO_3$ inert support. The temperature at which the aqueous medium is maintained during contact of the chlorine dioxide precursor with the catalyst can vary widely. Preferably, the temperature is in the range of 5° C. to 80° C., and preferably 5° C. to 50° C. Typically the process is carried out at ambient temperature. The pH of the aqueous medium is usually in the range of 1 to 8, preferably 4 to 8. Generally, the catalyst contact time with the chlorine dioxide precursor ranges from 0.01 to 20 seconds.

Chlorine dioxide precursors which may be employed in the practice of the present invention are those compounds capable of generating, releasing or being converted to chlorine dioxide when contacted with a catalyst formed of Pd (or Pd+Pt or Pd+Au) deposited on a MgO or $CaCO_3$ or $K_2CO_3$ support under the reaction conditions previously described. Any metal chlorite salt capable of generating chlorine dioxide can be utilized as the chlorine dioxide precursor. Preferably, alkali metal chlorites are used, especially sodium chlorite in an aqueous medium. The amount of chlorine dioxide precursor present in the aqueous medium can vary widely and will be dependent upon the amount of chlorine dioxide to be generated. For example, it has been found that the amounts of chlorine dioxide precursor present in the aqueous medium can range from 0.0001 to 30 weight %, preferably 0.0005 to 10 weight %. Preferably, a chlorine dioxide complex sold by Bio-Cide International, Inc. of Norman, Oklahoma under the trademark Purogene®, is used (described in U.S. Pat. No. 5,008,096, incorporated by reference in its entirety).

In order to be able to control the chlorine dioxide formed in the course of the catalytic reaction and to direct the flow of the chlorine dioxide, it is desirable to conduct the reaction in a space where the catalyst and precursor solution are kept separate until it is desired to generate the chlorine dioxide. Thus, for marketing the product, a two component package can be provided with suitable separation means and dispenser means to direct the flow of chlorine dioxide to the surface, object or material to be disinfected.

All kinds of contact lenses may be disinfected by utilizing chlorine dioxide produced by the catalysts of the present invention in a manner known in the art.

In accordance with a further embodiment of the present invention there is provided a two component package which separately contains the catalyst and the chlorine dioxide precursor.

Figure 5:
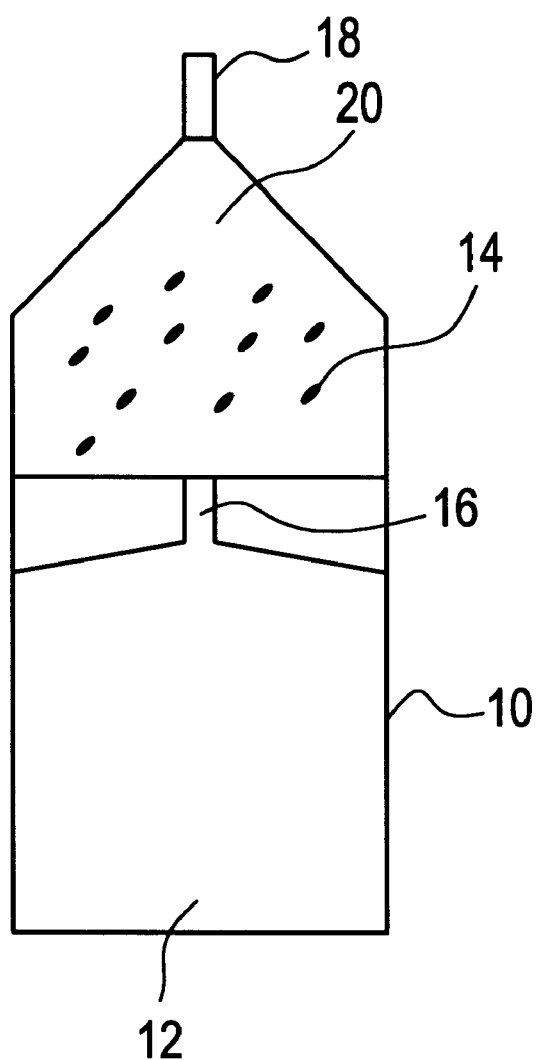
FIG. 5 is a schematic drawing of a multicompartment container which contains a chlorine dioxide precursor and the catalyst which generates chlorine dioxide from the precursor.

As shown in FIG. 5, there can be provided a device for dispensing chlorine dioxide 10 containing a compartment 12 for holding the aqueous precursor. The device also has a compartment 20 for holding the catalyst 14 separate and apart. from the aqueous precursor. A tube or other device 16 is arranged so as to permit contact of the aqueous precursor with the catalyst. A dispenser of any convenient design 18 can be arranged in the device 10 for delivery of the chlorine dioxide generated in the upper compartment 20.

Furthermore, the present invention concerns a method for generating chlorine dioxide from a chlorine dioxide precursor which utilizes the multicompartment container shown in FIG. 5. In order to generate chlorine dioxide, the container, for example, can be inverted and the compartment containing the chlorine dioxide precursor is squeezed in order to flow at least a portion of the chlorine dioxide precursor into the compartment which contains the catalyst. The resulting chlorine dioxide is ejected from the container via an opening to the surface of the item (e.g., contact lenses) to be disinfected or treated. The compartment which contains the catalyst is separated from the compartment containing the chlorine dioxide precursor by a catalyst retention means (e.g., a filter). The compartment which contains the catalyst is separated from the opening by a catalyst retention means (e.g., a filter).

EXAMPLES

The following examples are further illustrative of the present invention:

Example 1
Effect of Alloying Pd on Catalyst Activity

As shown in Table 1 and FIG. 1, the alloying of Pd with Pt, Ag or Au decreases the rate of deactivation (in comparison to a catalyst containing only Pd).

Catalyst K was prepared by suspending 48.3 grams of Rhone-Poulenc Chemie spheralite 532, a gamma alumina containing 1.3% $La_2O_3$ and 0.5% $Nd_2O_3$ and ground to a particle size range of 75 to 212 microns, in 250 ml of deionized water. To this suspension was added an aqueous solution of palladium nitrate containing 2.5 grams of Pd. The pH of the Pd solution had been adjusted to 1.0 with sodium carbonate. After heating this suspension at 80° C. for 15 min., while maintaining the pH at approximately 6–7 with sodium carbonate, a solution of sodium hydroxide and formaldehyde was added and the mixture stirred for another 15 min. The alumina containing 4.9 wt % reduced palladium was filtered, washed with DI water, and dried overnight at 120° C.

Catalyst L was prepared by suspending 94.7 grams of Rhone-Poulenc Chemie spheralite 532, a gamma alumina containing 1.3% $La_2O_3$ and 0.5% $Nd_2O_3$ and ground to a particle size range of 75 to 212 microns, in 500 ml of deionized water. To this suspension was added an aqueous solution of palladium nitrate and tetrachloro auric acid. This precious metal solution consisted of 5.0 grams of Pd and 2.0 grams of Au, and its pH had been adjusted to 1.0 with sodium carbonate. After heating this suspension at 80° C. for 15 min., while maintaining the pH at approximately 9–10 with sodium carbonate, a solution of sodium hydroxide and formaldehyde was added to the mixture stirred for another 15 min. The alumina containing 4.9 wt % reduced palladium and 2.0 wt % reduced gold was filtered, washed with DI water, and dried overnight at 120° C.

Catalyst M was made in the same manner as catalyst L except that the final catalyst consisted of 4.9% Pd and 3.0% Au.

Catalyst N was prepared by suspending 94.7 grams of Rhone-Poulenc Chemie spheralite 532, a gamma alumina containing 1.3% $La_2O_3$ and 0.5% $Nd_2O_3$ and ground to a particle size range of 75 to 212 microns, in 500 ml of deionized water. To this suspension was added an aqueous solution of palladium nitrate and platinum nitrate. This precious metal solution consisted of 5.0 grams of Pd and 2.0 grams of Pt, and its pH had been adjusted to 1.0 with sodium carbonate. After heating this suspension at 80° C. for 15 min., while maintaining the pH at approximately 6–7 with sodium carbonate, a solution of sodium hydroxide and formaldehyde was added and the mixture stirred for another 15 min. The alumina containing 4.9 wt % reduced palladium and 2.0 wt % reduced platinum was filtered, washed with DI water, and dried overnight at 120° C.

Catalyst O was prepared by suspending 95.2 grams of Rhone-Poulenc Chemie spheralite 532, a gamma alumina containing 1.3% $La_2O_3$ and 0.5% $Nd_2O_3$ and ground to a particle size range of 75 to 212 microns, in 500 ml of deionized water. To this suspension was added an aqueous solution of palladium nitrate and silver nitrate. This precious metal solution consisted of 5.0 grams of Pd and 1.1 grams of Ag, and its pH had been adjusted to 1.0 with sodium carbonate. After heating this suspension at 80° C. for 15 min., while maintaining the pH at approximately 9–10 with sodium carbonate, a solution of sodium hydroxide and formaldehyde was added and the mixture stirred for another 15 min. The alumina containing 4.9 wt % reduced palladium and 1.1 wt % reduced silver was filtered, washed with DI water, and dried overnight at 120° C.

Experiments were performed using catalysts K, L, M, N and O to determine their activity and stability to generate chlorine dioxide from an aqueous solution of sodium chlorite. In these tests 50 mg portions of the catalyst were held in a cylindrical cell at room temperature. An aqueous solution of sodium chlorite (150 ppm) was passed over the catalyst at a rate of approximately 1 ml/sec. The steady state concentration of $ClO_2$ generated in the outlet stream was measured each day over a three minute period. The concentration of $ClO_2$ was measured using an ultraviolet spectrometer in a manner known in the art.

TABLE 1

Effect of Alloying Pd with Pt, Ag and Au on Catalyst Activity

| Catalyst | K | L | M | N | O |
|---|---|---|---|---|---|
| Palladium, wt % | 4.9 | 4.9 | 4.9 | 4.9 | 4.9 |
| Gold, wt % | — | 2 | 3 | — | — |
| Platinum, wt % | — | — | — | 2 | — |
| Silver, wt % | — | — | — | — | 1.1 |
| Support Designation | 532 | 532 | 532 | 532 | 532 |
| $ClO_2$ Conc. (ppm): | | | | | |
| Initial | 2.75 | 2.99 | 2.81 | 3.39 | 2.54 |
| Day 15 | 0.75 | 1.49 | 1.78 | 2.01 | 1.38 |
| Day 30 | 0.4 | 1.03 | 1.55 | 1.32 | 0.94 |
| Deactivation, %: | | | | | |
| Day 15 | 72.7 | 50.2 | 36.7 | 40.7 | 45.7 |
| Day 30 | 85.5 | 65.6 | 44.8 | 61.1 | 63 |

By substituting Cu for Au or Ag (as shown in the preparation of catalysts L or M or O in Table 1), comparable results are obtained.

Example 2
Effect of Different Supports on Catalyst Activity

Catalyst P was made in the same manner as catalyst K except that the support was Aldrich 24,338-8, a commercially available source of MgO.

Catalyst Q was made in the same manner as catalyst L except that the support was Aldrich 24,338-8, a commercially available source of MgO.

Catalyst R was made in the same manner as catalyst N except that the support was Aldrich 24,338-8, a commercially available source of MgO.

Catalyst S was made in the same manner as catalyst M except that the support was Sturcal F, a commercially available source of $CaCO_3$ from Sturge Chemicals.

Catalyst T was made in the same manner as catalyst N except that the support was Sturcal F, a commercially available source of $CaCO_3$ from Sturge Chemicals.

The experiments to determine the activity and stability of catalysts P, Q, R, S and T for the generation of chlorine dioxide from sodium chlorite were performed in the same manner as described above.

Table 2 describes the MgO or $CaCO_3$ supports used for this catalytic system:

TABLE 2

Example 2 Support Descriptions

| Support Designation | 24,338-8 | Sturcal F | 532 |
|---|---|---|---|
| Material | MgO | $CaCO_3$ | Gamma $Al_2O_3$ |
| $La_2O_3$, wt % | — | — | 1.3 |
| $Nd_2O_3$, wt % | — | — | 0.5 |

TABLE 2-continued

Example 2 Support Descriptions

| Particle Size Range, μ | <200 | <200 | 75–212 |
|---|---|---|---|
| Pore Volume, cc/g | 1.7 E-2 | 1.7 E-2 | 7.2 E-1 |
| Surface Area, m²/g | 6.1 | 5.7 | 112 |

Table 3 describes the activity of these catalysts:

TABLE 3

Effect of Different Supports on Catalyst Activity

| Catalyst | P | Q | R | S | T |
|---|---|---|---|---|---|
| Palladium, wt % | 5 | 5 | 5 | 4.9 | 4.9 |
| Gold, wt % | — | 2 | — | 3 | — |
| Platinum, wt % | — | — | 2 | — | 2 |
| Support | MgO | MgO | MgO | CaCO$_3$ | CaCO$_3$ |
| ClO$_2$ Conc. (ppm): | | | | | |
| Initial | 0.69 | 0.92 | 0.92 | 1.12 | 1.38 |
| Day 15 | 0.29$^A$ | 0.72 | 0.89 | 0.98 | 1 |
| Day 30 | — | 0.37$^B$ | 0.6 | 0.8 | 0.69 |
| Deactivation, %: | | | | | |
| Day 15 | 58.0$^A$ | 21.7 | 3.3 | 12.5 | 27.5 |
| Day 30 | — | 59.8$^B$ | 34.8 | 28.6 | 50 |

$^A$This measurement was taken on day 14.
$^B$This measurement was taken on day 28.

Figure 2:
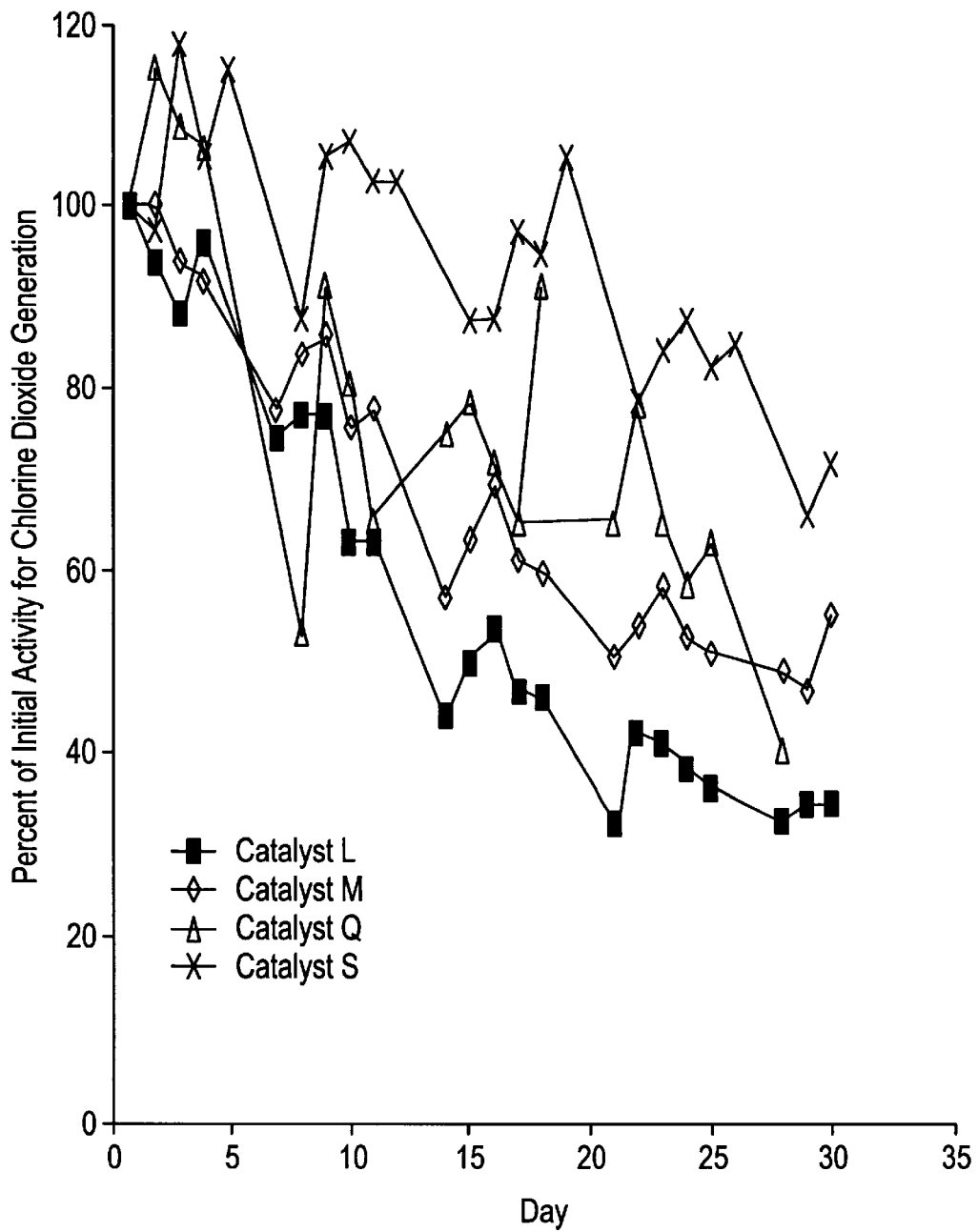
FIG. 2 is a graph of the effect of the support on Pd/Au catalysts.
Figure 3:
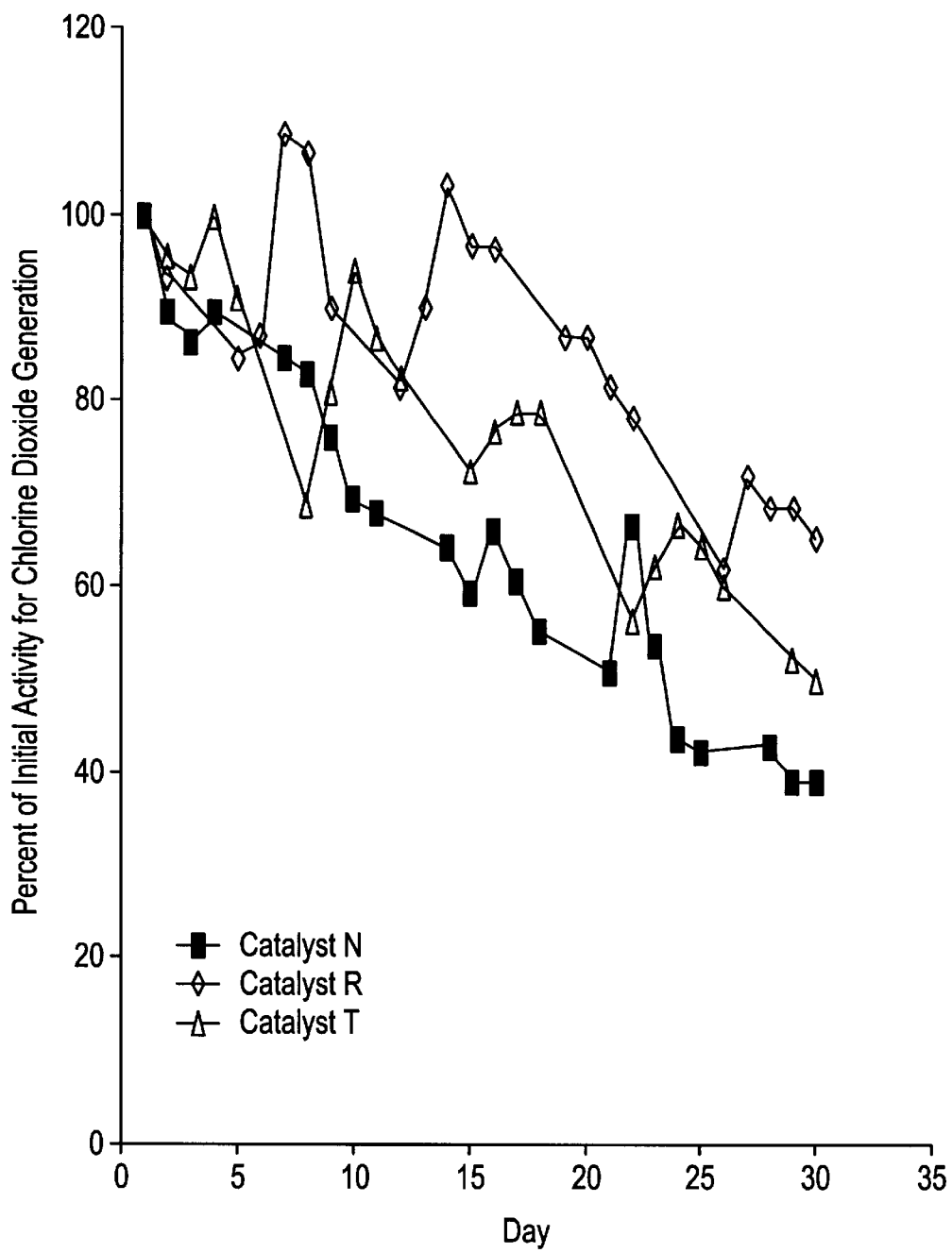
FIG. 3 is a graph of the effect of the support on Pd/Pt catalysts.
Figure 4:
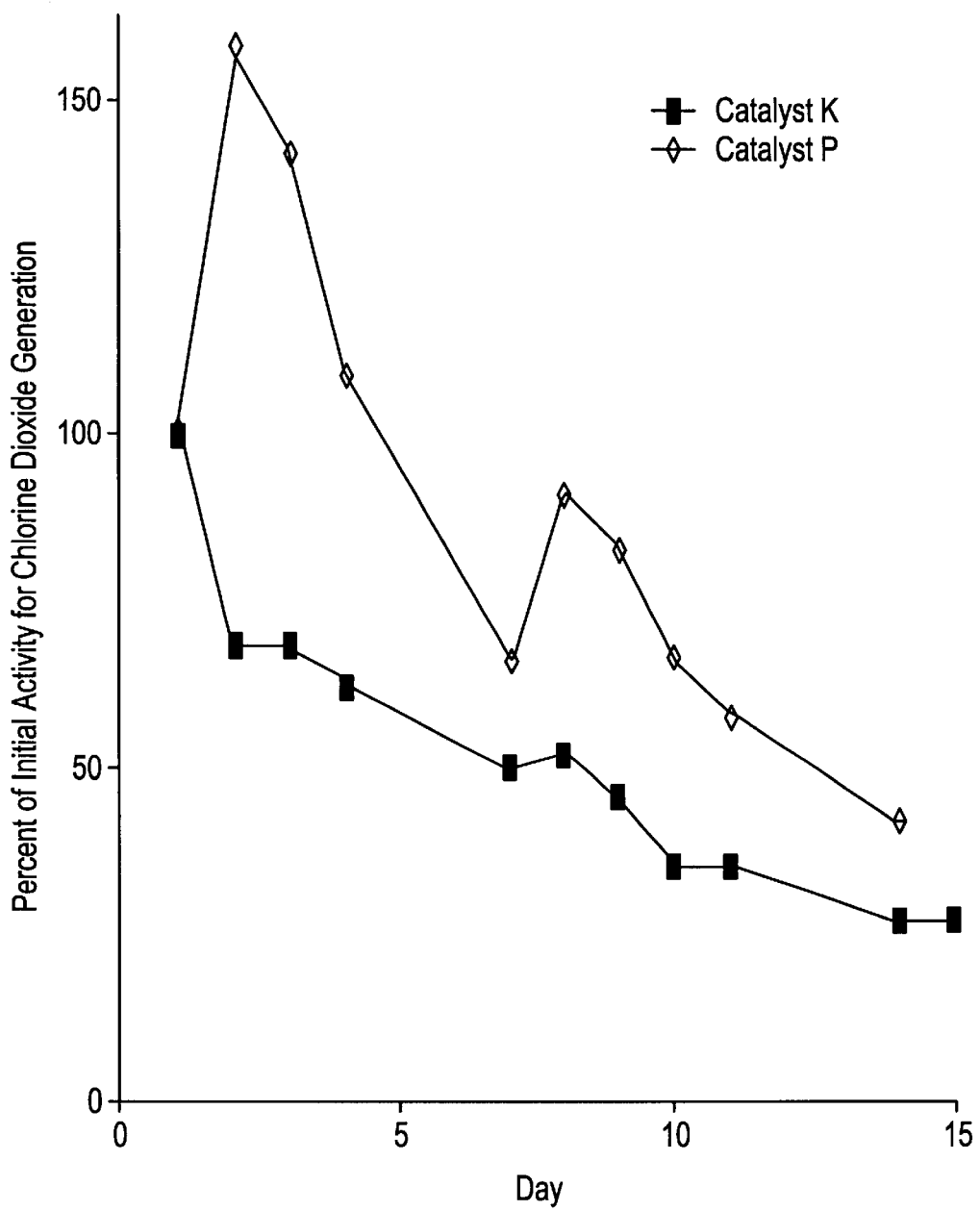
FIG. 4 is a graph of the effect of the support on Pd catalysts.

In comparing tables 1 and 3 it is obvious that the MgO and CaCO$_3$ supported catalysts, when compared to those on the Rhone-Poulenc Chemie spheralite 532, have lower levels of activity, but they deactivate less. Therefore, the MgO and CaCO$_3$ supported catalysts would be more desirable when low constant levels of ClO$_2$ generation are needed over an extended period of time. FIGS. 2, 3, and 4 show the effect of the different supports on the stability of the various Pd/Au, Pd/Pt, and Pd catalysts respectively.

Example 3

The Use of K$_2$CO$_3$ Modified 1/32" Alumina Spheres as a Support.

Table 4 and FIG. 6 demonstrate that a suitable catalyst can also be made on a K$_2$CO$_3$ modified fixed bed support. A 500 gram portion of the Condea 1/32" alumina spheres was modified by spraying on a solution that contained 10 g of K$_2$CO$_3$ and 215 grams of water. This was followed by a drying step at 100° C. in a rotating drum and an air calcination at 950° C. for one hour. As shown in Table 5, this modification has no noticeable effects on physical properties of the support.

TABLE 4

The performance of the K$_2$CO$_3$ modified 1/32" alumina spheres as a catalyst support

| Catalyst | U |
|---|---|
| Palladium wt % | 5 |
| Gold, wt % | 3 |
| Amount of K$_2$CO$_3$ Added, wt % | 2 |
| ClO$_2$ Conc. (ppm): | |
| Initial | 1.09 |
| Day 13 | 1.09 |
| Deactivation Day 13, % | 0 |

TABLE 5

The effects of the K$_2$CO$_3$ modification on the physical properties of the 1/32" alumina spheres

| Amount of K$_2$CO$_3$ Added, wt % | 0 | 2 |
|---|---|---|
| Surface Area, m²/g | 97.9 | 95.3 |
| Total Pore Volume, cc/g | 0.33 | 0.32 |
| Average Pore Diameter, Å | 133.5 | 133.7 |

Catalyst U was prepared by spraying 110.4 grams of the above mentioned K$_2$CO$_3$ modified Condea alumina 1/32" spheres with a 28.5 ml precious metal solution palladium as palladium chloride, 3.6 grams of gold as tetrachloroauric acid, 5 ml of 20% Na$_2$CO$_3$ solution. The catalyst was then reduced in a 20 ml solution comprised of 29.3% sodium formate and 2% hydrazine at 25° C. for 30 minutes. The catalyst was then filtered, washed with DI water, and dried overnight at 120° C.

The experiments to determine the activity and stability of catalyst U for the generation of chlorine dioxide from sodium chlorite was performed in the same manner as described in examples 1 and 2 except that 0.2003 grams of catalyst U was used. The cylindrical cell used to contain catalyst U during the experiments had the diameter of 4 mm and the height of 19 mm, while the cylindrical cell used for the catalysts of examples 1 and 2 had the diameter of 15 mm and the height of 1 mm.

Further variations and modifications of the invention will become apparent to those skilled in the art from the foregoing and are intended to be encompassed by the claims appended hereto.

U.S. Pat. Nos. 5,008,096; 4,731,192; and 4,362,707 are incorporated by reference in their entirety. Our copending U.S. patent application Ser. No. 08/008,971, filed on Jan. 26, 1993, now U.S. Pat. No. 5,435,984 issued on Jul. 25, 1995, is incorporated by reference in its entirety.

What is claimed is:

1. A catalyst having an exterior surface comprising palladium for producing chlorine dioxide, consisting essentially of a catalyst support selected from the group consisting of (a) a support modified by a Group IA carbonate salt or a Group IIA carbonate salt or MgO and (b) a support consisting of a Group IA carbonate salt or a Group IIA carbonate salt or MgO, wherein the exterior surface of said catalyst support is impregnated with palladium or palladium and another platinum group metal or palladium and a Group IB metal.

2. The catalyst according to claim 1, wherein said another platinum group metal is platinum.

3. The catalyst according to claim 1 wherein said Group IB metal is gold.

4. The catalyst according to claim 1, wherein said palladium is present in an amount of 0.1 to 20 weight % based on the total weight of said catalyst.

5. The catalyst according to claim 2, wherein said palladium and said platinum are present in an amount of 0.1 to 20 weight % based on the total weight of said catalyst.

6. The catalyst according to claim 2, wherein said palladium and said platinum are present in a ratio of Pt to Pd of 0.01:1 to 2:1.

7. The catalyst according to claim 6, wherein said palladium and said platinum are present in a ratio of Pt to Pd of 0.2:1 to 0.8:1.

8. The catalyst according to claim 3, wherein said palladium and said gold is present in an amount of 0.1 to 20 weight % based on the total weight of said catalyst.

9. The catalyst according to claim 3, wherein said palladium and said gold are present in a ratio of Au to Pd of 0.01:1 to 2:1.

10. The catalyst according to claim 9, wherein said palladium and said gold are present in a ratio of Au to Pd or 0.2:1 to 0.8:1.

11. The catalyst according to claim 1, wherein said Group IA carbonate salt is $K_2CO_3$.

12. The catalyst according to claim 1, wherein said Group IIA carbonate salt is $CaCO_3$.

13. The catalyst according to claim 1 wherein said modified support is a formed alumina modified with $K_2CO_3$ present in the amount of 2 to 50% by weight.

14. The catalyst according to claim 1 wherein said modified support is a high surface metallic or ceramic support.

15. The catalyst according to claim 14 wherein said modified support has a surface area of at least about 40 $m^2/g$.

16. The catalyst according to claim 14 wherein said modified support is gamma alumina, silica-alumina, silica, or titania.

17. The catalyst according to claim 1, said catalyst produced by a method consisting essentially of preadjusting the pH of an aqueous solution of (i) a palladium salt or (ii) a palladium salt and another platinum group metal salt or (iii) a palladium salt and a Group IB metal salt to a pH range of 1 to 6.3, adding said solution to a slurry of said catalyst support and water, maintaining the pH of said slurry from 6 to 10 at a temperature of 70° to 90° C., and adding a reducing agent, thereby impregnating the exterior surface of said catalyst support with palladium or palladium and another platinum group metal or palladium and a Group IB metal.

18. A method of making a catalyst for producing chlorine dioxide, said method consisting essentially of preadjusting the pH of an aqueous solution of (i) a palladium salt or (ii) a palladium salt and another platinum group metal salt or (iii) a palladium salt and a Group IB metal salt to a pH range of 1 to 6.3, adding said solution to a slurry of water and a catalyst support selected from the group consisting of (a) a support modified by a Group IA carbonate salt or a Group IIA carbonate salt or MgO and (b) a support consisting of a Group IA carbonate salt or a Group IIA carbonate salt or MgO, maintaining the pH of said slurry from 6 to 10 at a temperature of 70° to 90° C., and adding a reducing agent, thereby impregnating the exterior surface of said catalyst support with palladium or palladium and another platinum group metal or palladium and a Group IB metal.

* * * * *